United States Patent

Wang et al.

[11] Patent Number: 6,063,259
[45] Date of Patent: May 16, 2000

[54] MICROFABRICATED THICK-FILM ELECTROCHEMICAL SENSOR FOR NUCLEIC ACID DETERMINATION

[75] Inventors: Joseph Wang, Las Cruces, N. Mex.; Xiaohua Cai, Waltham, Mass.

[73] Assignee: New Mexico State University Technology Transfer Corporation, Las Cruces, N. Mex.

[21] Appl. No.: 08/872,953

[22] Filed: Jun. 11, 1997

Related U.S. Application Data

[60] Provisional application No. 60/019,559, Jun. 11, 1996.

[51] Int. Cl.[7] ................................................. G01N 27/26
[52] U.S. Cl. ........................................ 205/777.5; 204/403
[58] Field of Search .................... 204/403; 205/777.5, 205/792; 435/817

[56] References Cited

U.S. PATENT DOCUMENTS

| | | | |
|---|---|---|---|
| 4,348,477 | 9/1982 | Nakano et al. | 435/91.41 |
| 4,786,373 | 11/1988 | Salobeimo et al. | 205/789.5 |
| 5,091,299 | 2/1992 | Turner et al. | 435/4 |
| 5,096,669 | 3/1992 | Lauks et al. | 422/61 |
| 5,120,421 | 6/1992 | Glass et al. | 204/406 |
| 5,128,015 | 7/1992 | Szuminsky | 204/403 |
| 5,269,891 | 12/1993 | Colin | 205/777.5 |
| 5,292,423 | 3/1994 | Wang | 204/434 |
| 5,296,125 | 3/1994 | Glass et al. | 430/311 |
| 5,298,129 | 3/1994 | Eliash | 205/782 |
| 5,312,527 | 5/1994 | Mikkelsen et al. | 205/777.5 |
| 5,387,508 | 2/1995 | Jaffe | 435/32 |
| 5,389,215 | 2/1995 | Horiuchi et al. | 205/775 |
| 5,437,772 | 8/1995 | De Castro et al. | 205/775 |
| 5,494,562 | 2/1996 | Maley et al. | 104/403 |
| 5,512,489 | 4/1996 | Girault et al. | 205/777.5 |
| 5,776,672 | 7/1998 | Hashimoto et al. | 435/6 |

FOREIGN PATENT DOCUMENTS 0 569 908 A2   11/1993   European Pat. Off. .

OTHER PUBLICATIONS

Wang et al. ("Trace Measurements of RNA by Potentiometric Stripping Analysis at Carbon Paste Electrodes", Anal. Chem. 1995, 67, 4065–4070) Nov. 1995.

Wring et al. ("Chemically Modified, Screen–printed Carbon Electrodes*", Analyst, Aug. 1992, vol. 117, p.1281).

CAPLUS abstract of Palecek et al. ("Cyclic voltammetry of nucleic acids and determination of submicrogram quantities of deoxyribonucleic acids by adsorptive stripping voltammetry", anal. Chim. acta (1986), 187, 99–107) Month Unknown.

CAPLUS abstract of Palecek ("New trends in electrochemical analysis of nuceic acids", Bioelectrochem. Bioenerg. (1988), 20(1–30, 179–940 Month Unknown.

Hashimoto et al. ("Sequence–specific Gene Detection with a Gold Electrode Modified with DNA Probes and an Electrochemically Active Dye", Anal. Chem. vol. 66, No. 21, 3830–3833) Month Unknown, 1988.

Green, Monika J., and Paul I. Hilditch, "Disposable Single–Use Sensors," *Analytical Proceedings*, vol. 28, Nov. 1991, p. 374.

(List continued on next page.)

Primary Examiner—T. Tung
Assistant Examiner—Alex Noguerola
Attorney, Agent, or Firm—Deborah A. Peacock; Rod D. Baker; D. Goelet Kehl

[57] ABSTRACT

A thick-film sensing apparatus for nucleic acid determination and testing using potentiometric stripping analysis, including two methods for nucleic acid detection at the microfabricated strips, both methods being designed for use with the thick-film sensing apparatus. The present invention is applicable for broad use in nucleic acid analysis, particularly for measurement of nucleic acids (e.g., DNA and RNA), and their sequences and interactions, and for detection of DNA damage, at thick-film electrodes, based on stripping potentiometry.

20 Claims, 12 Drawing Sheets

OTHER PUBLICATIONS

Hall, Jennifer M., James Moore–Smith, Joe V. Bannister & John Higgins, "An Electrochemical Method for Detection of Nucleic Acid Hybridisation," *Biochemistry and Molecular Biology International*, vol. 32, No. 1, Jan. 1994, pp. 21–27.

Noble, Deborah, "DNA Sequencing on a Chip," *Analytical Chemistry*, vol. 67, No. 5, Mar. 1, 1995, pp. 201–204.

Ostapczuk, Peter, "Present Potentials and Limitations in the Determination of Trace Elements by Potentiometric Stripping Analysis," *Analytica Chimica Acta*, 273 (1993), pp. 35–40 Month Unknown.

Palecek, Emil, "Electrochemical Behaviour of Biological Macromolecules," *Biochemistry and Bioenergetics*, 13 (1988) p. 273 Only First Page Provided Month Unknown.

Rivas, G., and V.M. Solis, "Electrochemical Determination of the Kinetic Parameters of Mushroom Tyrosinase," *Biochemistry and Bioenergetics*, 29 (1992) pp. 19–28 Month Unknown.

Wang, Joseph, and Baomin Tian, "Mercury–Free Disposable Lead Sensors Based on Potentiometric Stripping Analysis an Gold–Coated Screen Printed Electrodes," unpublished research proposal, Sep., 1995.

Wang, Joseph, Xiaohua Cai, Gustavo Rivas, Haruki Shiraishi, Percio A.M. Farias and Narasaiah Dontha, "DNA Electrochemical Biosensor for the Detection of Short DNA Sequences Related to the Human Immunodeficiency Virus," *Analytical Chemistry*, vol. 68, No. 15, Aug. 1, 1996, pp. 2629–2634.

Wang, Joseph, Analytical Electrochemistry, Chapter 5, Electro Chemical Sensors, pp. 154–156, VCH Publishers, Inc., New York, 1994. Month Unknown.

Wang, Joseph, Decentralized Electrochemical Monitoring of Trace Metals: From Disposable Strips to Remote Electrodes, *Analyst*, vol. 119, May 1994, pp. 763–766.

Wang, Joseph, Emanuel Sucman and Baomin Tian, Stripping Potentiometric Measurements of Copper in Blood Using Gold Microelectrodes, *Analytica Chemica Acta*, 286 (1994) pp. 189–195. Month Unknown.

Wang, Joseph and A. Julio Reviejo, "Organic–Phase Enzyme Electrode for the Determination of Trace Water in Nonaqueous Media," *Analytical Chemistry*, vol. 65, No. 6, Mar. 15, 1993, pp. 845–847.

Wang, Joseph, and Baomin Tian, "Screen Prined Stripping Voltmmetric/Potentiometric Electrodes for Decentralized Testing of Trace Lead," *Analytical Chemistry*, vol. 64, No. 15, Aug. 1, 1992, pp. 1706–1709.

Wang, Joseph, "Adsorptive Stripping Votammetry—A New Electroanalytical Avenue for Trace Analysis," Journal of Research on the Nation Bureau of Standards, vol. 91, No. 3, May–Jun. 1988, pp. 489–491.

Wang, Joseph, *Stripping Analysis*, Chapter 2, Cathode Stripping, pp. 58–60, VCH Publishing, New York, 1985. Month Unknown.

Wangsa, Julie and Mark Arnold, Fiber–Optic Biosensors Based on the Fluorometric Detection of Reduced Nicotinamide Adenine Dinucleotide, *Analytical Chemistry*, vol. 60, No. 10, May 15, 1988, pp. 1080–1082.

Wring, Stephen and John P. Hart, "Chemically Modified, Screen–Printed Carbon Electrodes," *Analyst*, vol. 117, Aug. 1992, pp. 1281–1282.

"Oakton™ Electrascan" meter for trace levels of heavy metals, manufacture by Cole–Palmer Instrument Company, Chicago, Illinois, product information, Mar. 1991.

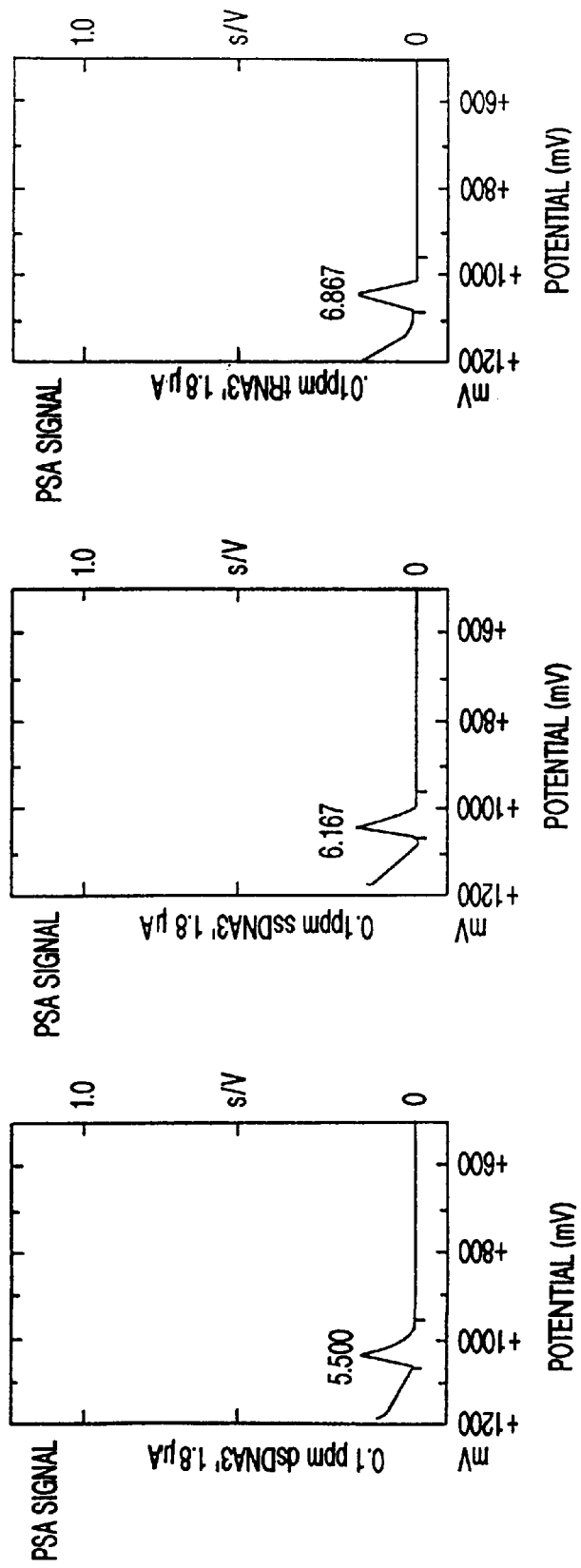

MICROFABRICATED THICK-FILM ELECTROCHEMICAL SENSOR FOR NUCLEIC ACID DETERMINATION

CROSS-REFERENCE TO RELATED APPLICATIONS

This application claims the benefit of the filing of Provisional Application Serial No. 60/019,559, entitled "Microfabricated Thick-film Electrochemical Sensor for Nucleic Acid Determination", filed on Jun. 11, 1996, and the specification thereof is incorporated herein by reference.

BACKGROUND OF THE INVENTION

1. Field of the Invention (Technical Field)

The present invention relates to methods and apparatus for nucleic acid determination, more particularly for measurement of nucleic acids (e.g., DNA and RNA), and their sequences and interactions, and for detection of DNA damage, at thick-film electrodes, based on stripping potentiometry.

2. Background Art

Thick-film technology is known to be useful for mass production of miniaturized electrochemical sensors (Prudenziati, S. "Thick-Film Sensors", *Elsevier*, Amsterdam (1994); Galan-Vidal, C., Muñoz, J., Dominguez, C. and Algeret, S., "Trends", *Anal. Chem.*, Vol. 14, p. 225 (1995); and Craston, D., Jones, D., Williams, D. and El Murr, N., *Talanta*, Vol. 38, p. 17 (1991)). The versatility of modem screen-printing processes, originally developed from microelectronics applications, has led to the automated and semi-automated fabrication of highly reproducible solid-state electrochemical transducers.

Most of the activity in this area has focused on the development of "one-shot" enzyme electrode strips for decentralized clinical testing of metabolites (Alvarez-lcarza, M. and Bilitewski, U., *Anal. Chem.*, Vol. 65, p. 525A (1993); Green, M. and Hildrich, P., *Anal. Proceed.*, Vol. 28, p. 374 (1991)), or field monitoring of pollutants (Kotte, H., Grundig, B., Vorlop, K. D., Strehilz, B. and Stottmeister, U., *Anal. Chem.*, Vol. 67, p. 65 (1995); Skladal, P., *Anal. Chim. Acta.*, Vol. 269, p. 281 (1992)). In addition to biocatalytic sensors, screen-printed electrodes have been fabricated for on-site stripping measurements of trace metals (Wang, J., Tian, B., *Anal. Chem.*, Vol. 65, p. 1529 (1992); Wang, J., *Analyst*, Vol. 119, p. 763 (1994); U.S. Pat. No. 5,292,423, entitled "Method and Apparatus for Trace Metal Testing", to Wang), or for electrocatalytic-amperometric detection of biomolecules, e.g., glutathione or ascorbic acid (Hart, J., Wring, S. A., *Electroanalysis*, Vol. 6, p. 617 (1994)).

There is a need for development of a low-cost miniaturized sensing device for the rapid detection of nucleic acids, their interactions, and more particularly their sequences. Such devices hold an enormous potential for early clinical diagnostics of genetically inherited diseases, on-site detection of food-contaminating organisms and forensic or environmental investigations. It is anticipated that both the speed and cost of such a DNA analytical test would be improved dramatically by miniaturization and microfabrication. Silicon-based (thin-film) microlithographic techniques have been explored by various companies for such development of DNA chips. (See Noble, D., "DNA Sequencing on a Chip", *Anal. Chem.*, Vol. 67, p. 201A (1995)).

Electrochemical techniques are known for being useful for nucleic acid analysis in general (Palacek, E., *Bioelectrochem. Bioenerg.*, Vol. 170, p. 421 (1988)), and for sequence-selective biosensing of DNA in particular (Millan, K. M. and Mikkelsen, S. R., *Anal. Chem.*, Vol. 65, p. 2317 (1993); Hashimento, K., Ito, K. and Ishimori, Y., *Anal. Chem.*, Vol. 66, p. 3830 (1994)). However, such early applications have relied on the use of conventional mercury drop or carbon and gold disk electrodes which are bulky and difficult to automate. Additionally, early operations have required time-consuming steps for completion of the task.

It is also known to detect nucleic acid hybridization by direct electrochemical techniques, including performing electrochemical analyses for detecting specific nucleic acids using carbon working electrodes combined with voltammetric procedures (Hall, J., Moore-Smith, J., Bannister, J., and Higgins, 1. J., "An Electrochemical Method for Detection of Nucleic Acid Hybridisation", *Biochemistry and Molecular Biology International*, Vol. 32, No. 1, p. 21 (1994)). A screen-printed electrode is shown in one instance in connection with the detection of hybridization (i.e. native (ds) versus denatured (ss) indicative of hybridization detection), again used with voltammetry. However, these methods and apparatus for DNA/RNA measurement are limited to use with very high concentrations of nucleic acids (e.g., 300 ng) and do not encompass the use of potentiometric stripping analysis (PSA) or related chronopotentiometry for monitoring nucleic acids at screen-printed electrodes, nor the detection of DNA interactions, sequences or damage.

There has been a need for developing reliable methods for detecting and quantifying the human immunodeficiency virus type 1 (HIV-1). The standard diagnostic test for HIV infection is an ELISA for the HIV antibody (in which viral antigens are adsorbed onto a solid phase). Western blot assays have also been used for this task. (Gallo, R., Montagnier, L., *Sci. Am.*, Vol. 259 (10), p. 41 (1988); Kuby, J., *Immunology*, Chapter 23, W. Freeman Inc., New York (1991); Nishanian, P., Huskins, K., Stehn, S, Deels, R., and Fahey, J., *J. Infect. Dis.*, Vol. 162, p. 21 (1990).) Alternately, nucleic acid hybridization schees have been proposed for detecting HIV-1 DNA sequences. These include radioisotopic assays, with the HIV probe labeled with the $^{32}p$ isotope or nonisotopic hybridization procedures employing calorimetric measurements. (Davis, G., Blumeyer, K., DiMichele, L., Whitfield, K., Chappelle, H., Riggs, N., Ghosh, S., Kao, P., Fhay, E., Kwoh, D., Guatelli, J., Spector, S., Richman, D., Gingeras, T., *J. Infect. Dis.*, Vol. 162, p. 13 (1990); Mulder, J., McKinney, N., Christopherson, C., Sninsky, J., Greenfield, L., Kwok, S., *J. Clin. Microbiol.*, Vol. 32, p. 292 (1994); Livache, T., Fouque, B., Teoule, R., *Anal. Biochem.* Vol. 217, p. 248 (1994); Rapier, J., Villamazo, Y., Schockeman, G., Ou, C., Brakel, C., Jonegan, J., Maltzman, W., Lee, S., Kirtiker, D., Galita, D., Clin. Chem., Vol. 39, p. 244 (1993).) Both of the hybridization strategies rely on prolonged (2-hour to 3-hour) hybridization times, with the isotopic assay complicated by the short half-life and hazardous nature of the radiolabeled probe. Also, although such solution-phase or bead-phase sandwich hybridization assays are suitable for diagnostic laboratories, there is an urgent need for faster, safer, cheaper, and easier-to-use hybridization sensors, based on the integration of DNA recognition layers and physical transducers, for decentralized screening (e.g., self-testing) of HIV-1 DNA.

There is also a long-term need for a rapid and user-friendly sensor for detecting damage to DNA in cells. Damage to DNA in cells leads to serious disturbance of the cell functions, usually involving minor variations in the DNA structure of conformation, and detection of such damage requires a highly sensitive analytical technique. Known procedures for measuring DNA damage rely on lengthy and insufficiently sensitive chromatographic or electrophoretic separation assays (Cadet, J., Weinfeld, M., *Anal. Chem.*, Vol. 65, p. 675A (1993)). In addition, such techniques cannot follow the dynamics of processes occurring in an exposure of DNA to physical or chemical damaging agents. Previous efforts in this area have used polarography for detecting DNA damage induced by exposure to ultraviolet or y radiation; however, since this strategy relies on mercury drop electrodes, it is not suitable for widespread sensing of DNA radiation damage (Vorlikova,., Palecek, E., Int. *J. Rad. Biol.*, Vol. 62, p. 363 (1974); Numberg, et al., Int. *J. Rad. Biol.*, Vol 42, p. 407 (1982)).

SUMMARY OF THE INVENTION
(DISCLOSURE OF THE INVENTION)

The present invention comprises a microfabricated thick-film sensor for trace measurements of nucleic acids (e.g., RNA and DNA), for monitoring their interactions and sequences, and for detection of DNA damage, and more specifically a microfabricated thick-film sensor designed for single-use decentralized measurements, and corresponding methods of microfabricating the thick-film sensor of the invention, based on stripping potentiometry at microfabricated screen-printed electrodes. The invention further comprises a new hybridization protocol for use with the sensors and the combination of the sensor in a compact, user-friendly, hand-held analyzer to fulfill the current requirements for decentralized DNA diagnostics.

A primary object of the present invention is to provide a microfabricated thick-film sensor for nucleic acid determination.

It is another object of the present invention to develop a low-cost miniaturized sensing device for the rapid detection of nucleic acids and their interactions and their sequences.

Another object of the invention is the coupling of the microfabricated nucleic acid sensor with a new hand-held, easy-to-use battery-operated instrument for on-site DNA diagnosis.

A further object of the invention is to avoid the previous need for bulky or toxic electrodes and time-consuming process steps.

Yet another object of the invention is to provide a rapid and simple method for nucleic acid detection at microfabricated strips.

A primary advantage of the present invention is that it provides a novel thick-film sensor comprising microfabricated electrode strips, which provides a performance that compares favorably to that of the previously known conventional, bulky or toxic electrodes, and which may be either disposable after a single use or reusable.

Another advantage of the present invention is that it provides two sensitive, rapid and simple methods for nucleic acid detection at the microfabricated strips of the thick-film sensor.

Yet another advantage of the invention is that it provides a computerized chronopotentiometric operation which addresses the high background response inherent to carbon surfaces and offers substantial lowering of the detection limit, not only compared to analogous voltammetric stripping measurements, but also in comparison to stripping voltammetry at mercury electrodes, thus providing convenient quantitation of nanogram (ng) amounts of DNA and RNA.

Yet another advantage of the sensor of the invention is that it's usefulness extends to testing and analysis for a wide variety of diseases (e.g., HIV and leukemia virus) and substances (e.g., pollutants and drugs).

A still further advantage of the invention is the provision of a simple, rapid and user-friendly method for routine centralized and decentralized testing of DNA.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings:

FIG. 5 shows stripping potentiograms for 100 $\mu$g/L dsDNA (A), 100 $\mu$g/L ssDNA (B), and 10 $\mu$g/L tRNA.

DESCRIPTION OF THE PREFERRED EMBODIMENTS (BEST MODES FOR CARRYING OUT THE INVENTION)

The present invention comprises a novel thick-film nucleic acid sensor which facilitates coupling the redox and the interfacial properties of nucleic acids for highly sensitive adsorptive stripping measurements. DNA and RNA spontaneously immobilizing onto the screen-printed electrode surface is used as an effective pre-concentration step, prior to a stripping determination using potentiometric stripping analysis. The sensor of the invention is a DNA/RNA sensor, having a nucleic acid-modified or -coated working electrode; various nucleic acids may be used as the modifier/coating, e.g., DNA, scDNA, RNA, tRNA. The nucleic acid-modified electrode may be a single or multiple array nucleic acid electrode. For example, if DNA is used as the modifier, the DNA may be double-stranded (dsDNA) for interaction reactions with, e.g., pollutants or drugs, or single-stranded (ssDNA) for hybridization (sequence specific) reactions.

Figure 1:
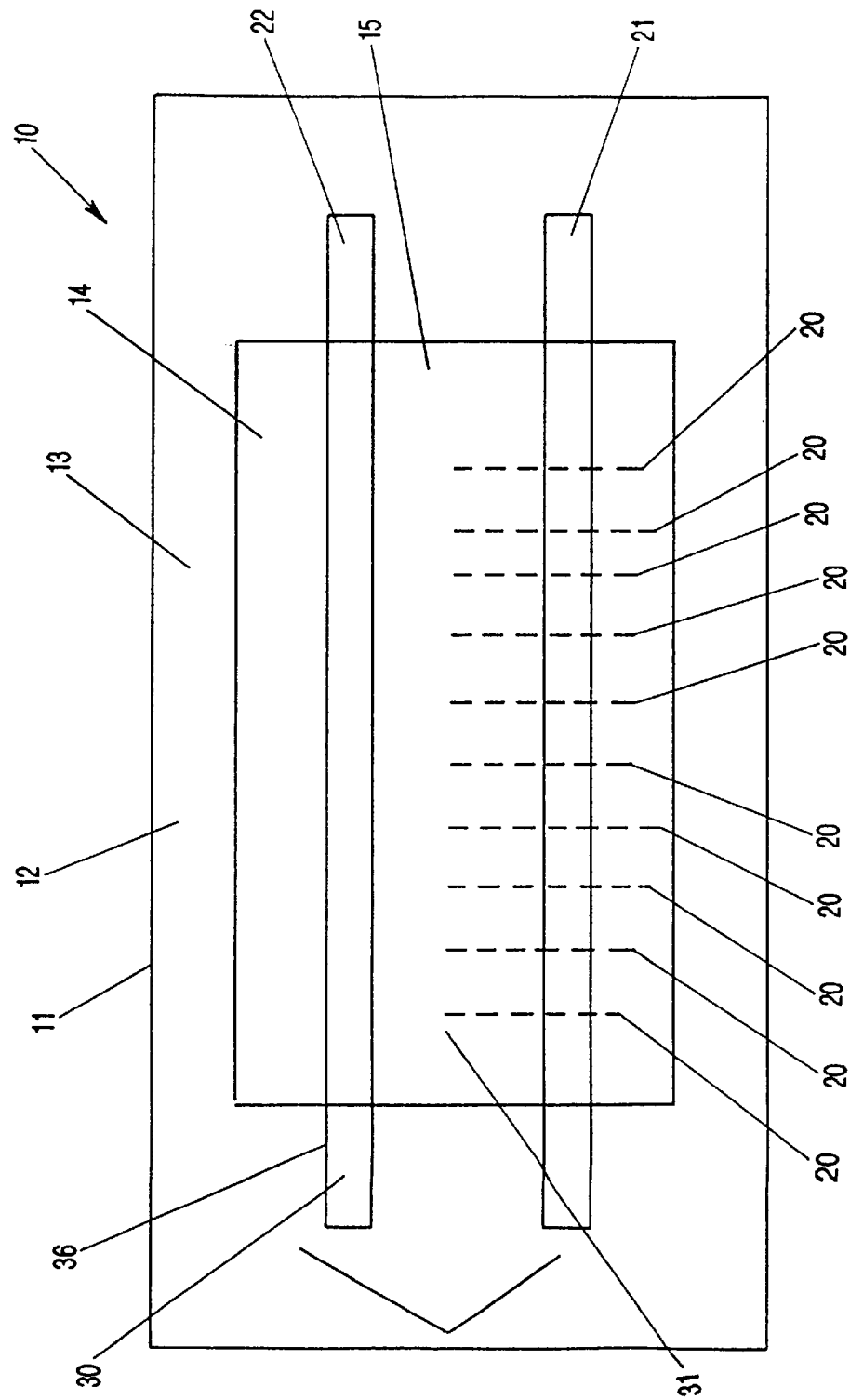
FIG. 1 is a top view of the preferred sensor of the invention.

FIG. 1 illustrates the preferred thick-film sensor 10 of the invention which is fabricated by using a semi-automatic screen printer (Model TF-100, MPM, Inc., Franklin, M. A.) to construct the working electrode strip 30. Carbon ink (Production No. C10903D4, Gwent Electric Materials, Ltd., U.K.) is used to print through a paftem stencil onto a 33 mm×100 mm alumina ceramic plate 11, having a top surface 12 (shown) and an opposite surface 13 (not shown). It should be particularly noted that other inks may be used for printing the working electrode, e.g., metal inks such as gold, platinum, etc., and the plate 11 may also be a formed of other materials than ceramics, e.g., a plastic substrate.

A plurality of electrode strips 20, e.g., a group of ten electrodes, each being 1.5 mm×30 mm, are thus printed onto plate 11 and subsequently dried for 60 minutes in an oven at 180° C. Reference electrode 21 and contact 22 to the working electrode 30 are also printed on plate 11. After a short cooling period, an insulator layer or cover 14 is placed onto part of the printed carbon area 15 (not shown) on plate 11, leaving a defined 1.5 mm×5 mm working electrode 30 in a working area 31 of the plate 11 and a similar area 36 (not shown) for electrical contact on the opposite surface 13 of plate 11. It should be particularly noted here that the sensor of the invention may be a two-electrode (reference electrode and working electrode) system or a three-electrode (reference electrode, auxiliary electrode and working electrode) system.

Advantageously, the response of the thick-film sensor is reproducible. This was evaluated from a series of 14 repetitive measurements of 1 mg/L tRA following a 1-minute accumulation. A stable PSA peak was observed throughout this series (RSD=6.9%; range +54–64 ms; mean=61 ms). Therefore, in addition to single-use applications, the sensor may be structured as a reusable device, since no apparent carryover is observed upon sweeping between nucleic acid solutions of low and high concentrations. The pretreatment/accumulation/stripping cycle makes the sensor fully reversible. For example, alternating between 5 and 0 mg/L ssDNA solutions for 4 cycles yields a stable response for the 5 mg/L solution and no response for the 0 mg/L solution. Measurements of 5 mg/L ssDNA were also used for assessing the strip-to-strip reproducibility. A group of 10 electrodes from the same plate thus yielded a relative standard deviation of 4.4%.

The present invention further comprises two sensitive, rapid and simple methods for nucleic acid detection at the microfabricated strips, both methods being designed for use with the novel thick-film sensor of the invention. The first preferred method (Method 1) involves direct potentiometric stripping measurements of extremely low levels of DNA and RNA following their adsorptive accumulation onto the strip surface. The second alternative method (Method 2) relies on the use of hybridization recognition events at a probe-coated strip electrode for sequence-selective biosensing.

In both methods of the invention, potentiometric stripping analysis (PSA) is employed to follow the oxidation of either the adsorbed nucleic acid species (Method 1) or the hybridization events (Method 2). In particular, constant current potentiometric stripping analysis (ccPSA) is used for measuring remarkably low levels (picogram (pg)) levels of nucleic acids at the carbon-based electrodes. Selected parameters of the fabrication process and the PSA operation allow convenient monitoring of sub-microgram per liter nucleic acid concentrations. Detection limits are 3 mg/L for tRNA, 25 mg/L for ssDNA, and 30 mg/L for dsDNA. Unlike analogous voltammetric monitoring of the adsorbed nucleic acid, which suffers from a large background current at the high potential associated with the oxidation of the guanine moiety, the computerized PSA operation offers a nearly flat baseline, thus enabling substantially lower detection limits. As desired for single-use applications, such operation eliminates the need for the previously-used (toxic) mercury-drop electrodes and related time-consuming deaeration steps.

The Method 1 procedure is the following: new strips are rinsed thoroughly with sterile double-distilled water prior to their immersion in the cell; each measurement cycle consists of a 60-second anodization at +1.8 V, followed by accumulation from a stirred (300 rpm) solution, for a period depending on the nucleic acid concentration, and using a potential of +0.5 V; the potentiostat is then disconnected; and the accumulated nucleic acid is oxidized by passage of a constant anodic current (usually +1.8 $\mu$A).

Method 2 comprises modifying the strips of the sensor of the invention for nucleic acid hybridization. Nucleic acid hybridization is a fundamental analytical technique for detecting specific DNA or RNA sequences. The strong adsorption of single stranded nucleic acids onto the surface of the microfabricated strips results in stable coated electrodes that are used for recognizing complementary strands of nucleic acids. Other modes of accumulation may also be used (e.g., covalent attachment). According to Method 2, after the initial adsorption, the strip electrode, with the accumulated nucleic acid, is immersed in another solution containing the target strand and uses PSA for transducing the base pairing recognition event.

Hybridization-based sequence detection is accomplished by accumulating poly(G) or oligo(dG)$_{20}$ onto the electrochemically pre-treated carbon strip sensor from a stirred solution containing these probes. The accumulation proceeds for one minute, while holding the electrode at +0.5 V. The coated strip is then washed with water and transferred to the stirred sample solution, containing the complementary poly(C) or oligo(dC)$_{20}$ targets. The hybridization reaction proceeds for a short period (10 second to 10 minute) while holding the electrode at +0.5 V. The hybrid is then detected by constant-current PSA.

An alternative embodiment of the thick-film sensor of the invention is the sequence-selective hybridization chip(s) resulting from the Method 2 modification of the thick-film sensor with single-stranded oligonucleotides. In testing (discussed below), the surface-bound probes on the single stranded nucleic acid-modified strips were found to selectively hybridize with their complementary ssDNA or ssRNA. The hybridization was detected directly by changes in the guanine-oxidation peak of the immobilized probe. Alternatively, a redox indicator (e.g., an electroactive metal complex) associated with the duplex can be used for the detection.

Strong, irreversible adsorption is essential for accomplishing such a hybridization assay for which the alternative embodiment was designed. The stability of the nucleic acid modified electrode was examined by monitoring its PSA response in a blank electrolyte solution in a manner analogous to the adsorptive transfer stripping protocol at mercury electrodes. No apparent loss in the PSA response of the oligo(dG)$_{20}$- or the poly(G)-modified electrodes was observed after their immersion in a stirred blank solution for periods of 10, 20, and 30 minutes, while holding potential at +0.5 V. The positively charged surface of the electrodes facilitates the retention of the negatively charged nucleic acids.

The thick-film sensor of the invention may be used as an electrochemical biosensor for the rapid detection of short DNA sequences related to the human immunodeficiency virus type 1 (HIV-1). The sensor relies on the accumulation and hybridization of the 21- or 42-mer single-stranded ologonucleotide from the HIV-1 U5 long terminal repeat (LTR) at carbon or strip electrodes (the transducers), their hybridization with the coplementary sequence targets, binding of the tris(1,10-phenanthroline)cobalt [Co(ohen)33+] marker to the hybrid, and chronopotentiometric monitoring of the hybridization process (via the increased marker peak). The extent of hybridization between the complementary sequences is determined by the enhancement of the chronopotentiometric peak of the Co(phen)$_3^{3+}$ indicator. Numerous factors affecting the probe accumulation, target hybridization, and indicator binding reactions must be controlled to maximize the sensitivity and speed the assay time.

The use of the new thick-film sensor in this application allows direct quantification of nanomolar concentrations of the target HIV-1 U5 Ltr sequence following short (10 minute-to-30 minute) hybridization times. More specifically, a detection limit of $4\times10^{-9}$ M HIV-1 U5 LTR segment has been reported following a 30-minute hybridization. Also, advantageously, the hybridization biosensor format obviates the use of radioisotopes previously used in radioactive methods for the detection of HIV-1 DNA. Further, direct adsorptive chronopotentiometric stripping measurements of trace levels of various HIV-1 DNAs have been obtained using the sensor of the invention. Results of testing of the sensor of the invention in this application are discussed in FIG. 10 below.

The thick-film sensor of the invention may be used as an electrochemical biosensor for the rapid detection of radiation-induced DNA damage. In this application, the sensor employs a dsDNA-coated screen-printed electrode and relies on changes in the guanine-DNA oxidation signal upon exposure to ultraviolet (UV) radiation. The changes in the intrinsic DNA oxidation response are induced by exposure to UV radiation for the sensing of the DNA damage. The decreased signal is ascribed primarily to conformational changes in the DNA and to the photoconversion of the guanine-DNA moiety to a nonelectroactive monomeric base product. Factors influencing the response of these microfabricated DNA sensors include irradiation time, wavelength, and distance. FIG. 11 (discussed later) illustrates the results of testing the use of the sensor for this application.

In yet another embodiment of the invention, the operation of the microfabricated DNA strips is combined with a hand-held, battery-operated, potentiometric stripping analyzer (not shown); the compact (4×7") instrument has been developed in connection with decentralized blood-lead testing. It consists of a potential control, current source and the single computer board. Built-in software controls the entire sequence of events, including the pretreatment/adsorption/ stripping cycle, data handling and display which is on a liquid crystal.

The present invention having been generally described, the following examples are provided to illustrate some of the properties and demonstrate the practical advantages thereof, and to allow one skilled in the art to utilize the present invention to its fullest extent. These examples included are to be construed as merely illustrative, and not limitative of the remainder of the disclosure or the claims in any way whatsoever.

Industrial Applicability:

The thick film sensors of the present invention were fabricated and tested, and the associated methods of the present invention were performed using the following equipment and conditions. The analytical protocol for of the invention employs short (30-second to 120-second) accumulation periods for an effective interfacial accumulation of the nucleic acid, followed by a constant-current stripping (measurement) step (ccPSA). As seen in the discussion of the FIGURES below, monitoring of the potential against the time results in a sharp peak associated with the oxidation of the bound guanine residue.

The effect of several experimental variables on the nucleic acid stripping response was evaluated and optimized. Microfabrication conditions had a profound effect on the PSA response. Various commercial carbon inks (Gwent (U. K.) and Ercon or ESL (USA)) were compared for this task; the Gwent ink yielded the most favorable performance. Different ink drying temperatures and periods were examined with 60 seconds at 180° C. offering the best performance.

The following biochemicals were used as reagents and were obtained from Sigma Chemical Company: double-stranded calf thymus DNA (dsDNA, activated and lyophilized, Catalog No. D4522); single-stranded calf thymus DNA (ssDNA, lyophilized powder, Catalog No. D8899); transfer RNA (tRNA from baker's yeast, lyophilized powder, Catalog No. R8759), polyguanylic acid (5') (poly(G), potassium salt, lyophilized, Catalog No. P4404); polycytidylic acid (5') (poly(C), potassium salt, Catalog No. P4903); and diethylpyrocarbonate (DEPC, Catalog No. D5758). The oligo(dG)$_{20}$ (ammonium salt, Primer No. A0162E08) and oligo(dC)$_{20}$ (ammonium salt, Primer No. A0162E09) were provided by Life Technologies (Grand Island, N.Y.).

Aqueous media used for preparing the RNA solutions (tRNA, poly(G) and poly(C)) were treated with 0.1% DEPC for 12 hours at 37° C. and were subsequently autoclaved for 30 minutes. All other solutions were prepared with sterile double-distilled water. The supporting electrolyte was 0.2 M acetate buffer solution (pH 5.0).

A TraceLab potentiometric stripping unit (PSU 20, Radiometer, Denmark) and an IBM PS/2 55SSX computer were used to obtain the potentiograms shown in the FIGURES set out below. Some experiments were carried out using a hand-held, battery-operated, potentiometric stripping analyzer indicating the adaptability of the methods and sensor of the invention to on-site, decentralized measurement. The three electrode system (all three electrodes having been screen-printed on the same chip) for the potentiometry consisted of the screen-printed electrode (SPE) strip, the silver/silver chloride (Ag/AgCl) reference electrode (Model RE-1, BAS) and the platinum wire auxiliary electrode, although again, a two-electrode system (eliminating the auxiliary electode) may be used. In the practice of the invention, none of the electrodes used are limited to these particular materials, i.e., Ag/AgCl or Pt. The electrode joined the 2 mL cell through holes in its Teflon cover. The cell, and all glassware and containers with the exception of the electrodes, were sterilized by autoclaving for 30 minutes.

A diode array spectrophotometer (Model 8452A, Hewlett Packard) was employed for measuring the concentration of the nucleic-acid stock solution (at 260 nm).

The invention is further illustrated by the following non-limiting examples.

EXAMPLE 1

Figure 2A:
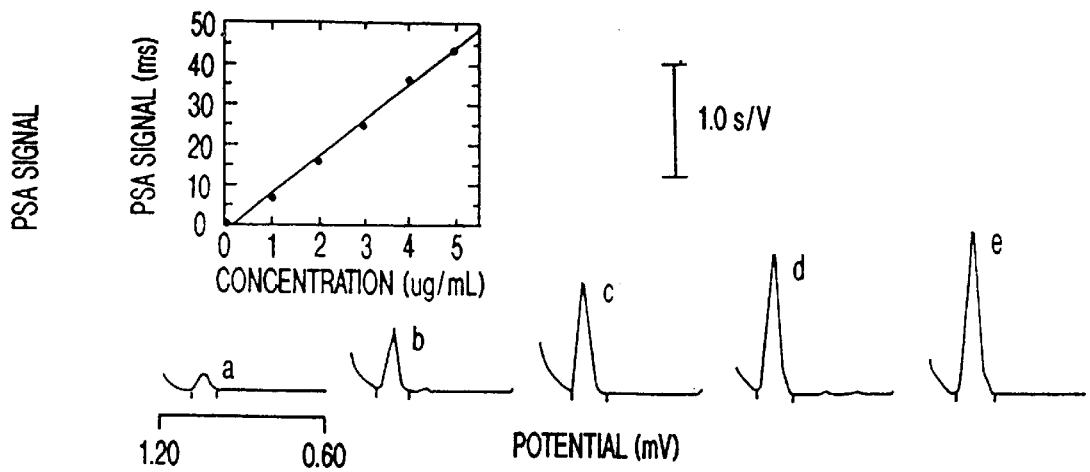
FIG. 2 illustrates the PSA response of the thick-film sensor of the present invention to solutions of increasing levels of dsDNA (A), ssDNA (B) and tRNA (C).
Figure 2B:
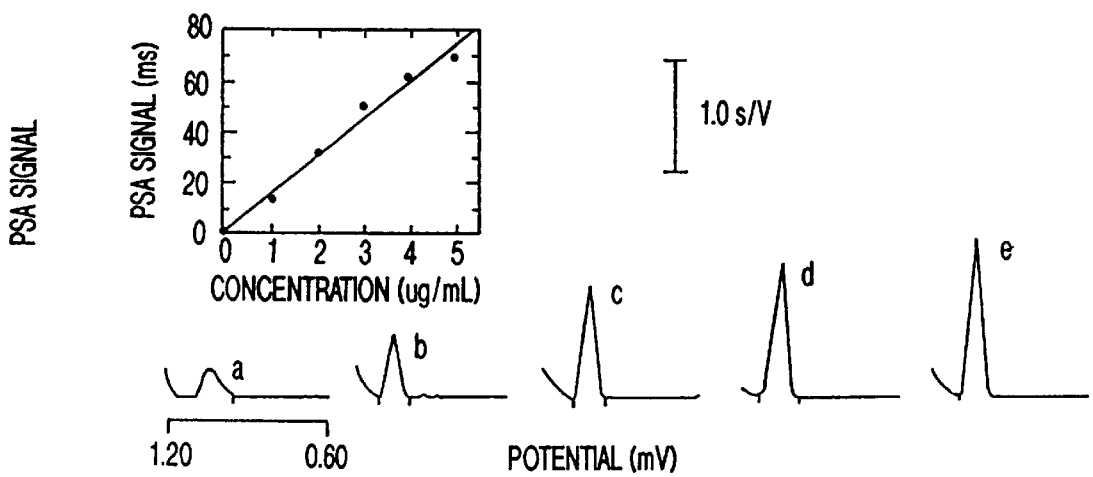
Figure 2C:
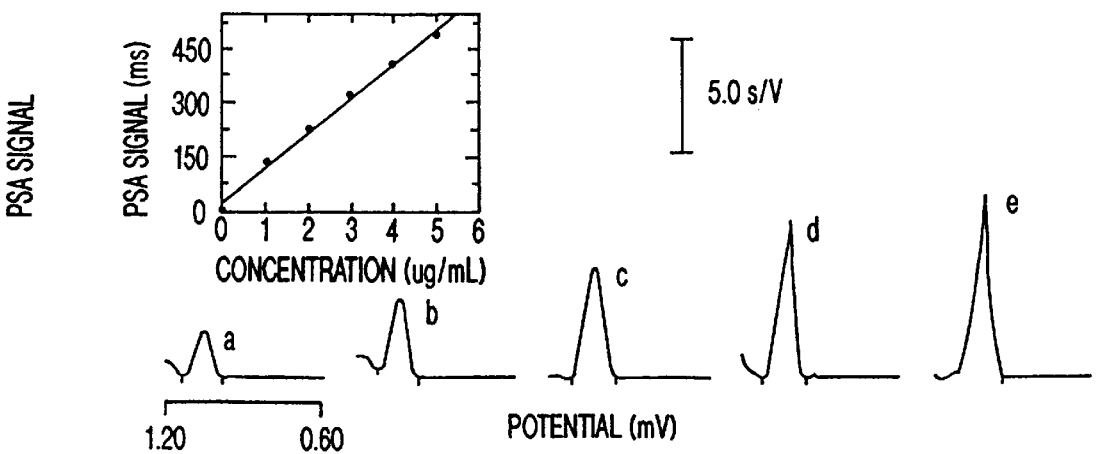
Figure 3A:
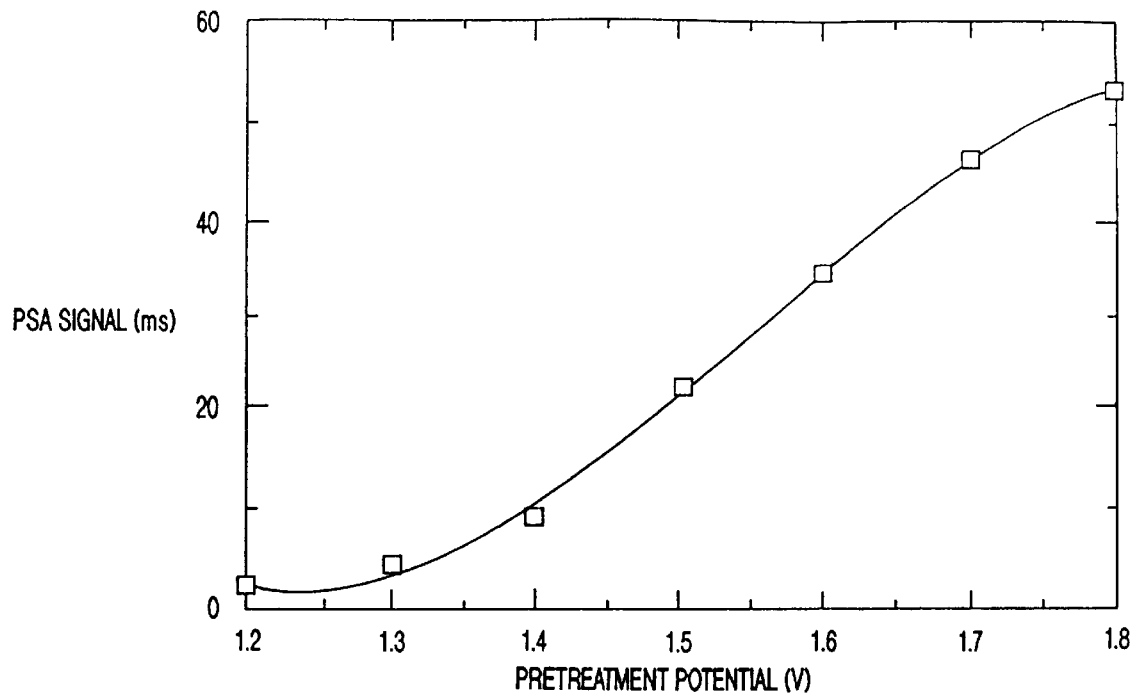
FIG. 3 illustrates the influence of the pre-treatment potential (A), pretreatment time(B), accumulation potential (C), and stripping current (D) on the response of the thick-film sensor of the invention to 5 mg/L ssDNA at one-minute accumulation.
Figure 3B:
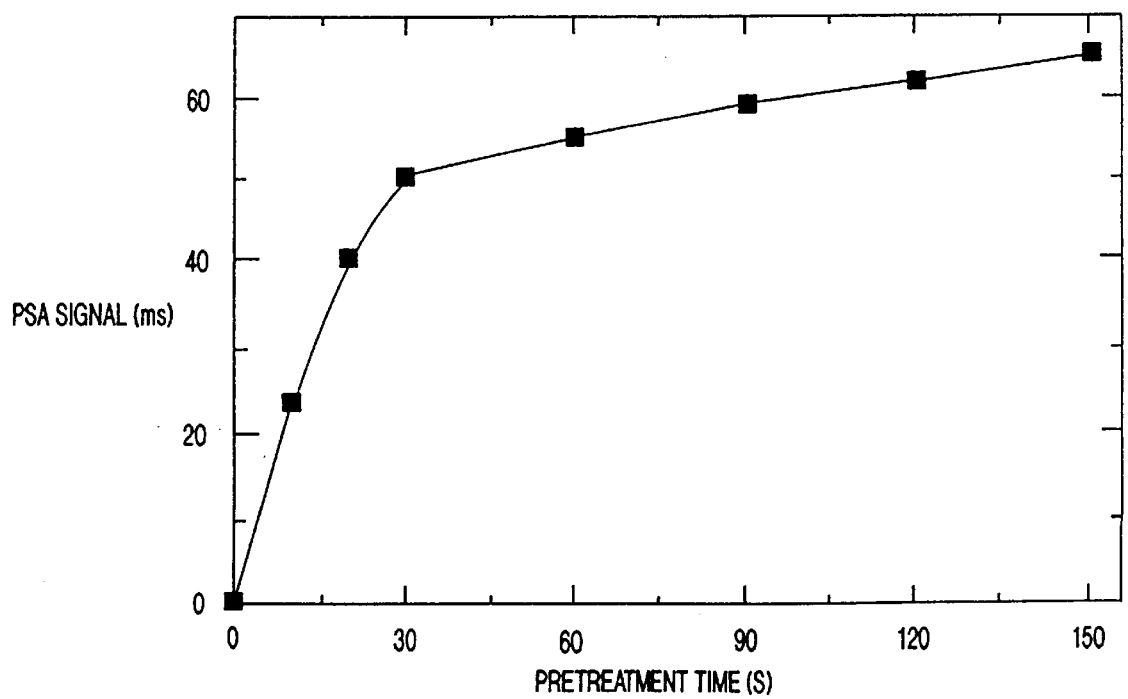
Figure 3C:
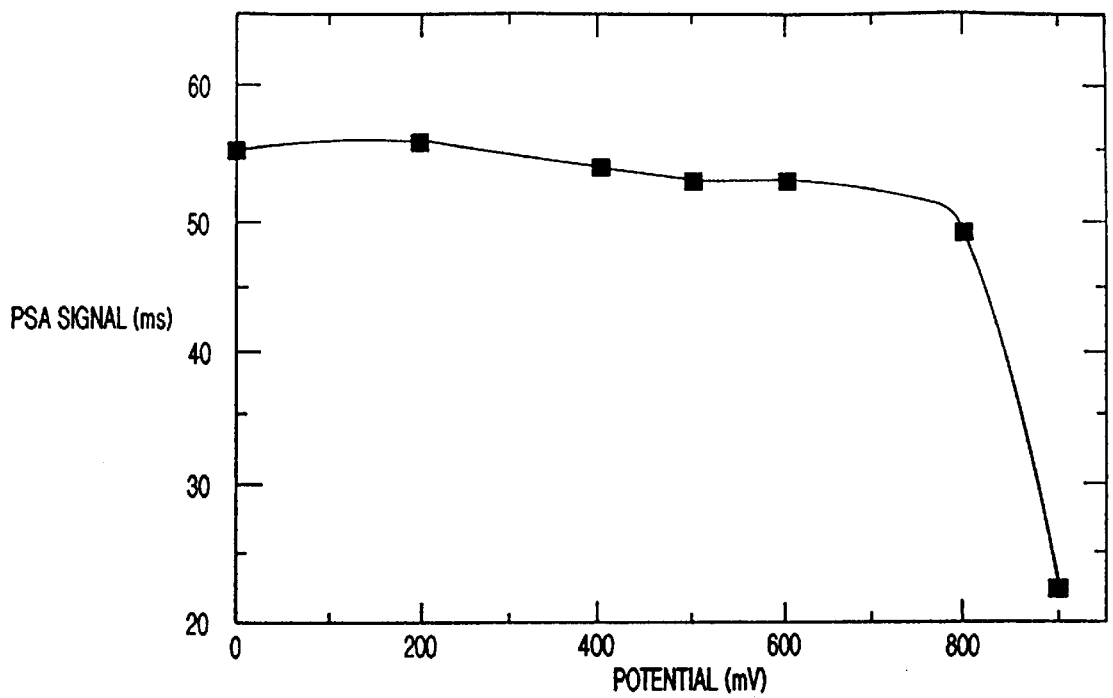
Figure 3D:
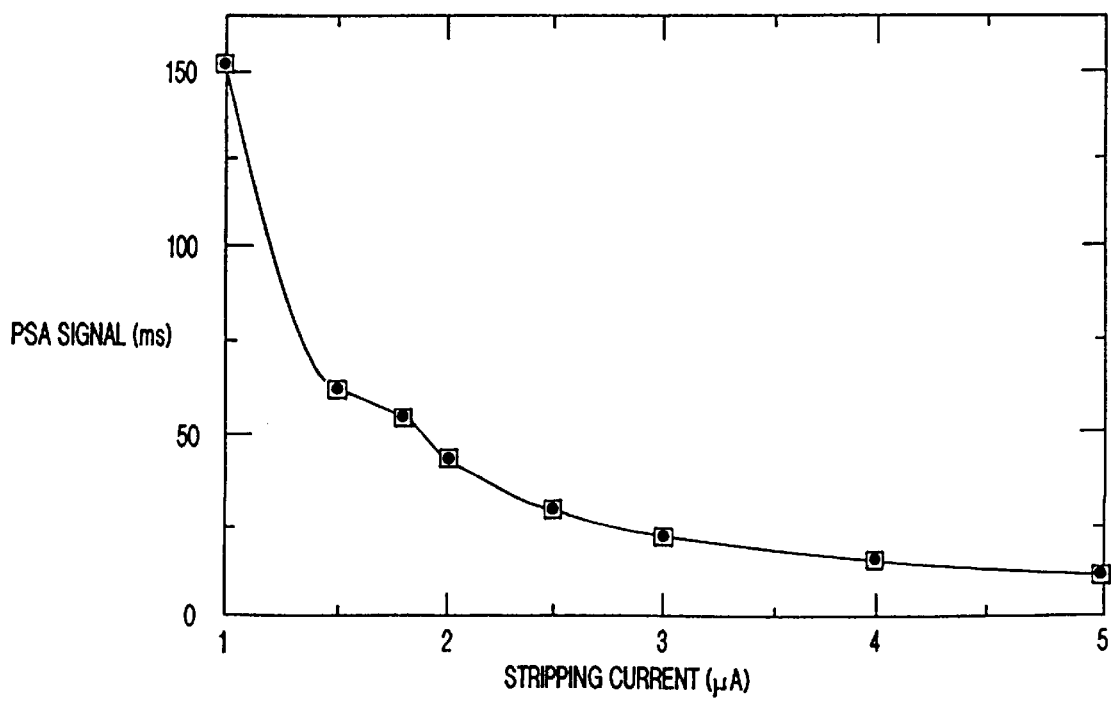

FIG. 2 illustrates the PSA response of the thick-film sensor to solutions of increasing levels of dsDNA (A), ssDNA (B), and tRNA (C) in 1 mg/L steps; more particularly, the FIGURE displays the PSA response of the microfabricated strips for solutions of increasing concentration (1–5 mgs/L, a–e, of dsDNA(A), ssDNA(B) and tRNA (C), respectively). The test was performed with one minute accumulation (at +0.5 V) followed by a constant current (1.8 $\mu$A) stripping. The electrode pre-treatment consisted of one minute at +1.8 V. The solution was 0.2 M acetate buffer (pH 5). Also shown as insets are the resulting calibration plots.

Oxidation of the bound guanine base yielded well-defined peaks ($E_p$=+1.02 V) over this concentration range. Convenient quantitation of all nucleic acids can thus be accomplished despite the very short (1 minute) accumulation time and the very high peak potential. The guanine oxidation peak increased linearly with the nucleic acid concentration as seen in the inset for the resulting calibration plot. Least-squares treatment of these plots yielded slopes of 9.16 for dsDNA, 14.51 for ssDNA, and 96.3 for tRNA ms.L/$\mu$g (correlation coefficients, 0.996, 0.984, and 0.996, respectively). Overall, the data of FIG. 2 indicated that the disposable strips function in a manner comparable to conventional, bulky, carbon paste electrodes with no compromise in the signal-to-noise characteristics as discussed in connection with the detection limit data below.

EXAMPLE 2

The influence of various experimental variables affecting the response and operation of the fabrication process and the PSA operation were tested. In testing, it was found that the screen-printed electrodes required a short electrochemical activation prior to each measurement. FIG. 3 illustrates the influence of the pretreatment potential (A), pretreatment time(B), accumulation potential (C), and stripping current (D) on the response of the thick-film sensor of the invention to 5 mg/L ssDNA at one minute accumulation. The FIG. 2 parameters were also used in these experiments for following: the pretreatment time used to obtain plots A, C, and D; the pretreatment potential used to obtain plots B, C, and D; the accumulation potential used to obtain plots A, B, and D; the stripping current used to obtain plots A, C, and C; and the electrolyte.

With respect to the effect of the pre-treatment time (A) and potential (B), respectively, upon the response to 5 mg/L ssDNA, the PSA signal increases slowly upon raising the activation potential between +1.2 and +1.4 V, and then more rapidly up to +1.8 V. A very sharp increase in the DNA response was observed upon changing the pre-treatment time from 0 and 30 sec. with a slower increase thereafter. A 1-minute activation at +1.8 V was employed throughout this study. Such pre-treatment appears to increase the hydrophilic character of the printed carbon surface and hence to facilitate the adsorptive accumulation. A similar activation step was employed for analogous measurements at carbon paste electrodes.

The influence of the accumulation potential (C) and stripping current (D) is also shown in FIG. 3. The response was nearly independent of the pre-concentration potential between 0.0 V and +0.6 V, and decreased sharply above +0.8 V (upon approaching the peak potential). The ssDNA peak decreased rapidly upon increasing the stripping current between +1.0 $\mu$A and +2.5 $\mu$A and then more slowly. A potential of +0.5 V and a current of +1.8 $\mu$A were therefore selected for most subsequent work.

EXAMPLE 3

Figure 4:
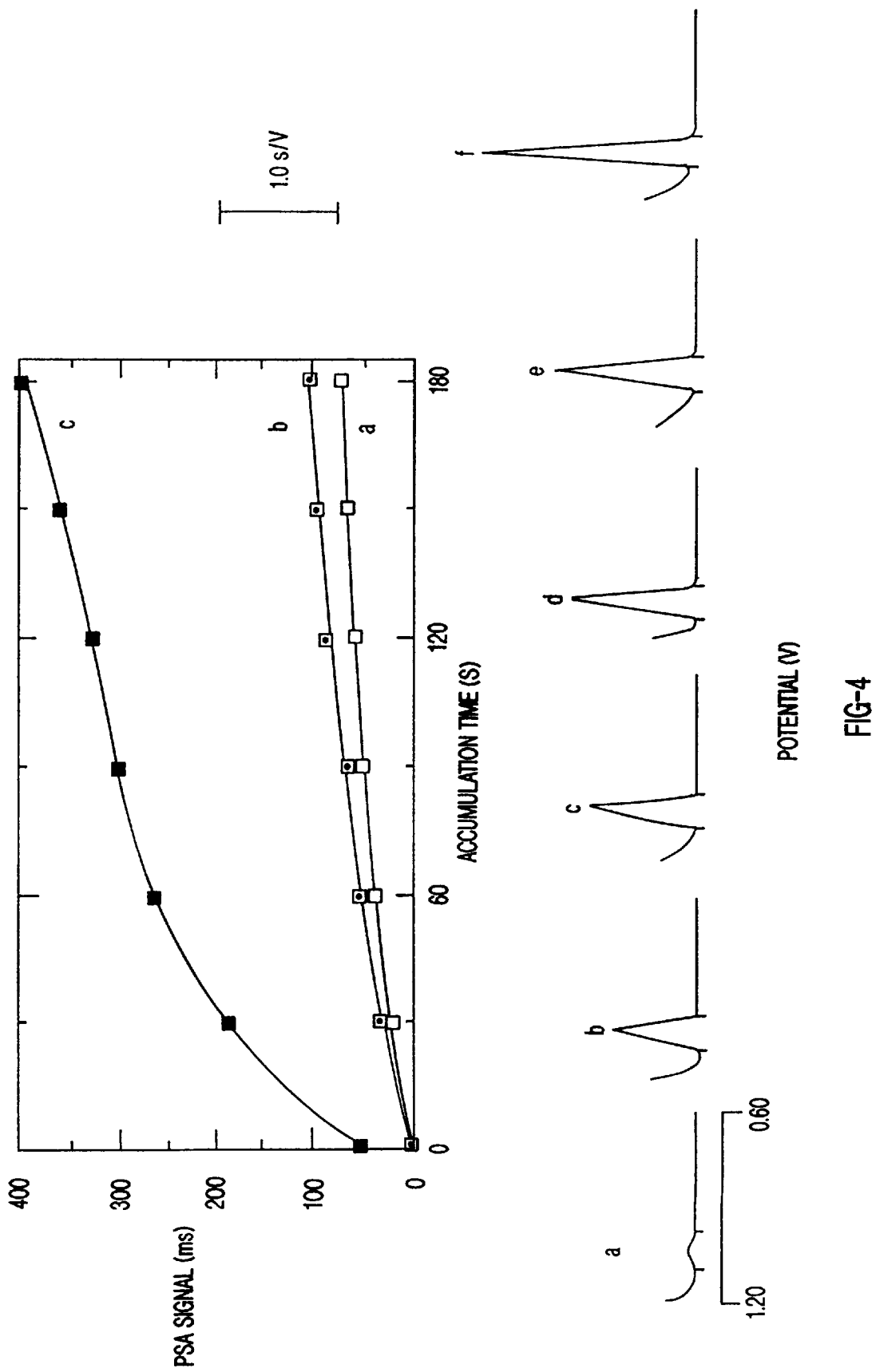
FIG. 4 is a stripping potentiogram for 5 mg/L dsDNA following different accumulation times, with inset plots of stripping time versus accumulation periods for dsDNA (a), ssDNA(b) and tRNA (c).

In testing, it was also found that the sensor response toward nucleic acids is strongly dependent upon the pre-concentration period. FIG. 4 displays stripping potentiograms for 5 mg/L dsDNA after different pre-concentration periods ranging from 1 second (a), 60 seconds (b), 90 seconds (c), 120 seconds (d), 150 seconds (e) and 180 seconds (f). Other than pre-concentration periods, other conditions used were those detailed for obtaining the plots of FIG. 2. Also shown as insets are plots of the stripping time versus the accumulation period for 5 mg/L dsDNA (a), ssDNA (b) and tRNA (c).

The longer the pre-concentration time, the more DNA is adsorbed onto the screen printed surface, and the larger is the PSA signal. For example, 1-minute and 3-minute pre-concentration periods yielded 15- and 30-fold peak enhancements, respectively, relative to that obtained with 1-second accumulation.

The inset for FIG. 4 also shows the dependence of the response on the pre-concentration time for dsDNA (a), ssDNA (b) and tRNA (c). For adsorption-controlled processes, the nucleic acid peaks increase rapidly with time at first and then level off. The trend in sensitivity at the different accumulation times, tRNA>ssDNA>dsDNA, agreed with the calibration data shown in FIG. 2. The significantly higher sensitivity towards tRNA reflects the stronger adsorption of shorter nucleic acids onto carbon surfaces. Similarly, higher sensitivity was observed toward oligo(dG)$_{20}$ relative to polyG (not shown). The number of guanine bases appears to play a secondary role in the PSA response, compared to the length of the nucleic acid molecule.

The accumulation step was facilitated by forced convection (solution stirring). For example, 50% and 70% losses in the intensity of the response to oligo(dG)$_{20}$ or ssDNA, respectively, were observed using a quiescent solution. In view of the excellent sensitivity of the SPA protocol, and as desired for many decentralized applications, convenient quantitation of mg/L solutions can be readily accomplished using unstirred media.

EXAMPLE 4

With short pre-concentration times, the thick-film PSA sensor offers extremely low detection limits. FIG. 5 shows typical stripping potentiograms for 100 $\mu$g/L dsDNA (A) and 100 $\mu$g/L ssDNA (B), as well as for 10 $\mu$g/L tRNA (C), following a 3-minute accumulation time. All other conditions duplicated those in the testing for FIG. 2. Detection limits of 3 $\mu$g/L tRNA, 25 $\mu$g/L ssDNA and 30 $\mu$g/L tRNA are estimated based on the favorable signal-to-noise characteristics of these data (S/N=3). Such values correspond to 6 ng, 50 ng and 60 ng (tRNA, ssDNA and dsDNA, respectively) in the 2 mL solutions. Even lower mass detection limits are anticipated upon using longer accumulation periods and smaller sample volumes.

EXAMPLE 5

The operation of the microfabricated DNA strips was tested in combination with a hand-held, battery-operated, potentiometric stripping analyzer, comprising a 4-inch×7-inch instrument having potential control, current source and a single computer board. Built-in software controlled the entire sequence of events, including the pretreatment/adsorption/stripping cycle, data handling and display (e.g., on a liquid crystal). The choice of user-friendly software was made to minimize the need for operator training and facilitate decentralized DNA testing.

Figure 6B:
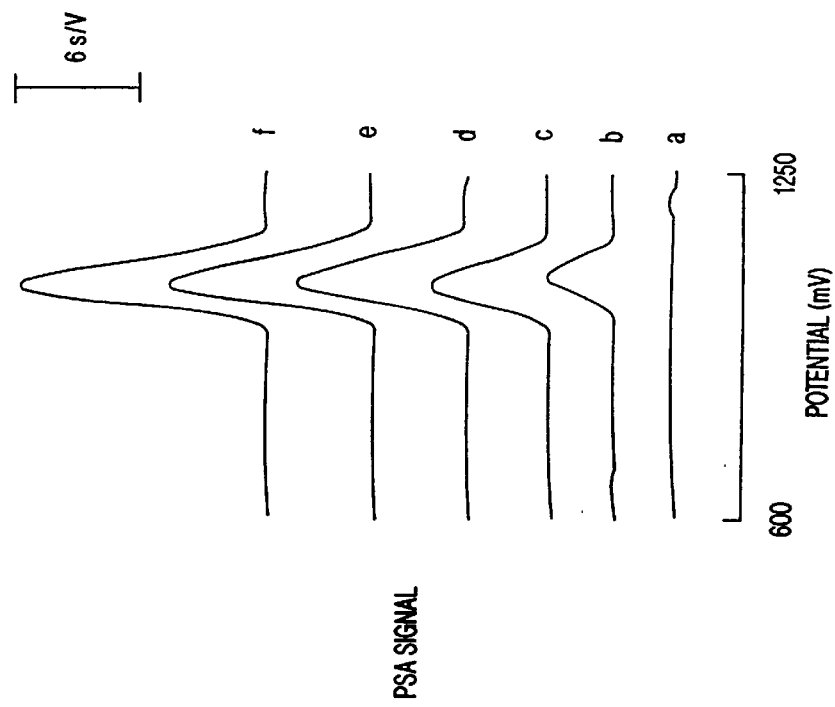
FIG. 6 provides graphs of nucleic acid detection using the nucleic acid sensor of the present invention with the hand-held PSA unit.
Figure 6A:
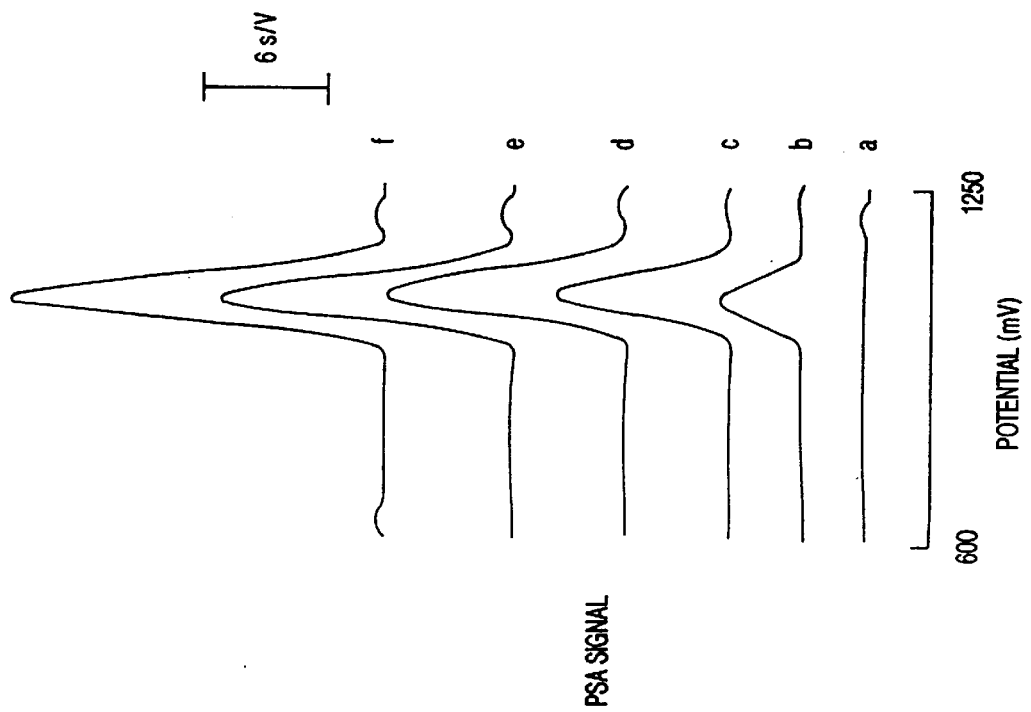

FIG. 6 displays nucleic acid detection with the hand-held PSA unit, more specifically, the PSA response of the instrument to tRNA (A) and ssDNA (B) solutions of increasing concentration in 0.2-mg/L and 1.0 mg/L increments (b–f), respectively, along with the background potentiograms (a). Conditions were the same as those used the testing for FIG. 2, except that here a 2-minute accumulation time and a two-electrode system were used.

In these tests, well-defined peaks and a low background were observed, in a manner analogous to those obtained with the larger Tracelab unit, which was the apparatus used in performing the experiments resulting in FIGS. 2–5. The performance tested covered the data processing function, including the signal digitization, data smoothing and baseline fitting. The resulting calibration plots were linear, with slopes of 97.0 ms.L/mg (A) and 11.7(B) ms.L/mg (correlation coefficients, 0.998 and 0.990, respectively).

EXAMPLE 6

Figure 7:
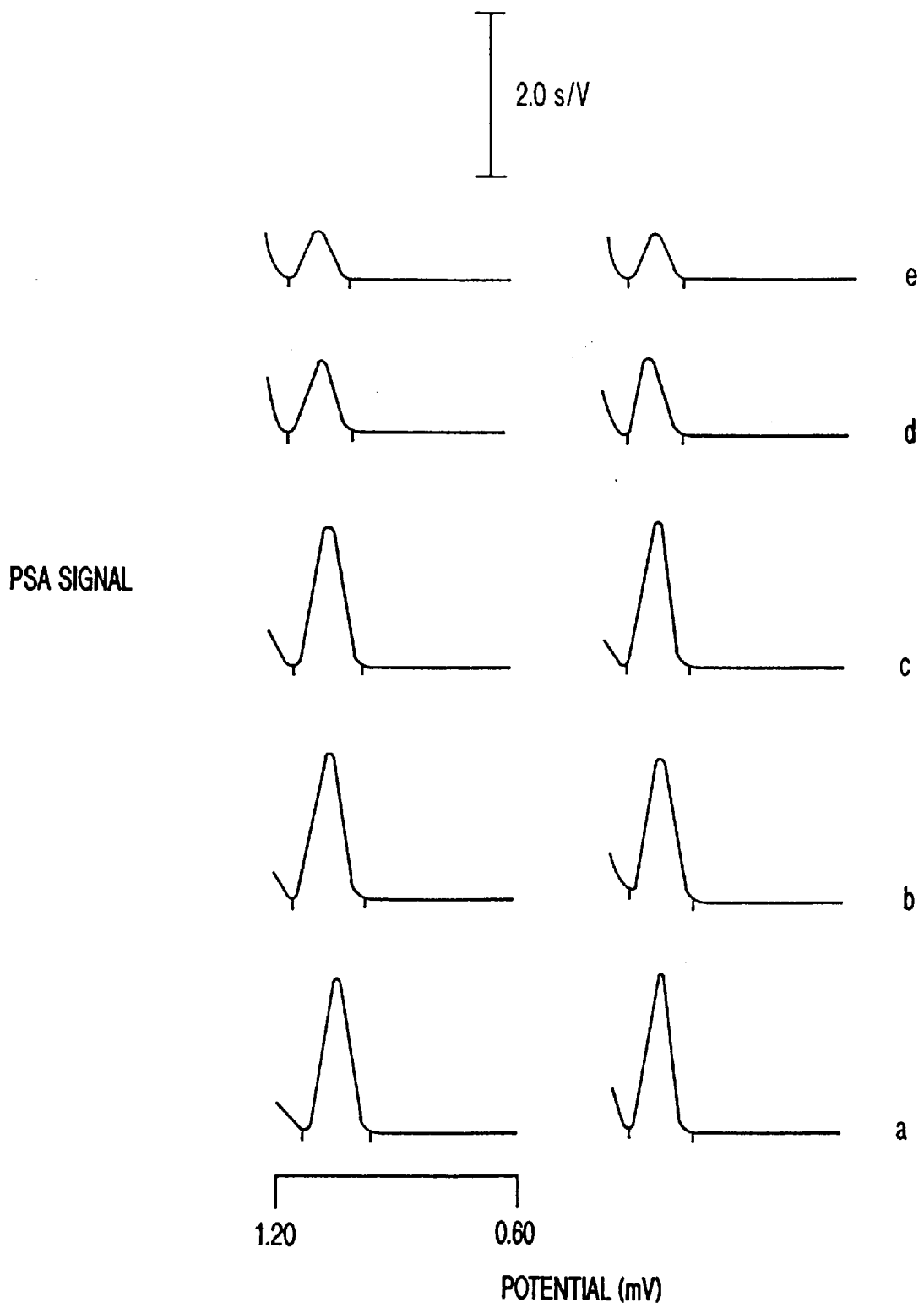
FIG. 7 provides graphs of the PSA response of a poly (G)-coated strip electrode in various solutions (a, b, c, d, and e).

The ability of the alternative embodiment of the thick-film sensor, the probe-modified strip, to respond selectively to its complementary strand is illustrated in FIG. 7. FIG. 7 shows the PSA response of the poly(G)-coated strip electrode in the blank solution (a), and following additions of 5 mg/L poly(U)(b), 5 mg/L poly(A)(c), and poly(C), 5 mg/L (d) and 10 mg/L (e). The poly(G)-modified electrode was prepared by immersing the pre-treated strip in a stirred buffer solution containing 2 mg/L poly(G) for one minute, while holding the electrode at +0.5 V. Hybridization time was 2 minutes at +0.5 V, and stripping current was 5 $\mu$A.

The non-complementary poly(U) and poly(A) had no effect on the guanine oxidation peak (b, c vs. a), indicating the absence of non-specific binding or competitive adsorption. In contrast, the poly(G)-modified electrode responded to successive additions of the poly(C) complement; the hybrid was detected directly by using the decrease of the guanine peak of the immobilized probe, without any redox-active intercalator/indicator. In another control experiment, poly(dA) and poly(dT) had no effect upon the response of the poly(G)-modified electrode (not shown).

EXAMPLE 7

Figure 8A:
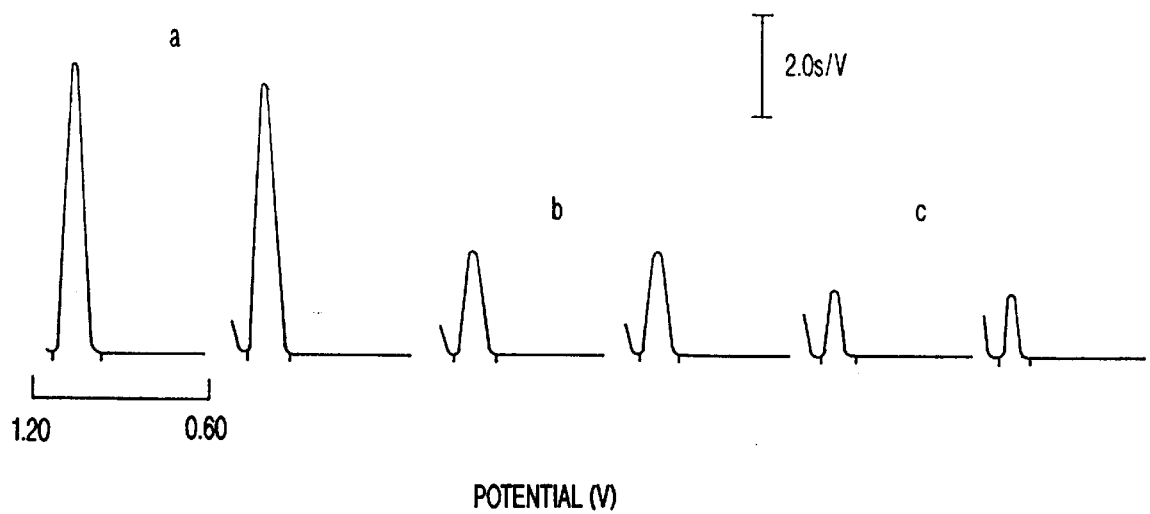
FIG. 8 shows the effect of the hybridization time on the PSA response of a poly(G)-coated strip electrode.
Figure 8B:
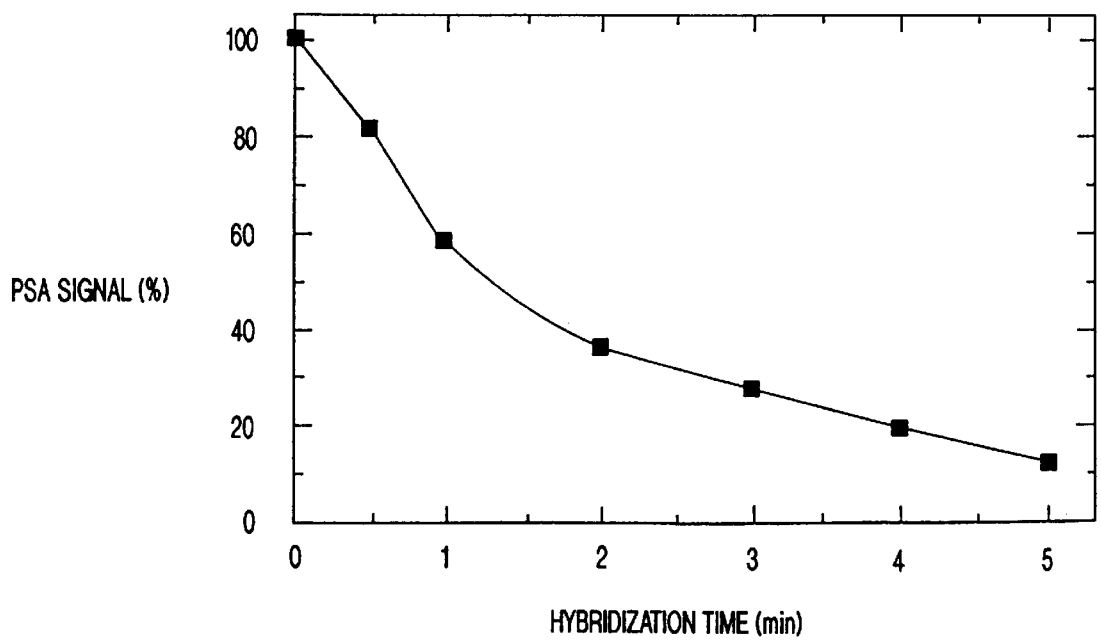

The extent of hybridization, and therefore the sensitivity of the nucleic acid-modified thick-film sensor, is strongly dependent upon the duration of the hybridization reaction. FIG. 8 displays the influence of the hybridization time upon the PSA response of the immobilized probe, specifically, the effect of the hybridization time on the PSA response of the poly(G)-coated strip. FIG. 8(A) displays the PSA peaks obtained after 0 minutes (a), 2 minutes (b) and 4 minutes (c) of stirring in the 5 mg/L target (poly(C)) solution. FIG. 8(B) is a plot of the relative PSA peak area vs. hybridization time. For this experiment, poly(G) concentration in the accumulation solution was 5 mg/L. Other conditions duplicated those in FIG. 7.

As shown in FIG. 8, the guanine peak decreased rapidly to 40% of its original value upon extending the hybridization time to 2 minutes and then more slowly. Relatively short hybridization times were sufficient for detecting extremely low levels of the target strand. For example, a detection limit of 0.09 mg/L (i.e., 90 ng) poly(C) was estimated from the change of the guanine peak of the poly(G)-coated strip following a 5-minute exposure to a 0.5 mg/L poly(C) solution (not shown). Substantially lower detection limits are anticipated in connection to amplification techniques, such as PCR.

EXAMPLE 8

FIG. 9 displays potentiograms, and resulting calibration plots, obtained at the poly(G)-modified electrode (a) and the oligo(dG)$_{20}$-modified electrode (b) in the presence of increasing levels of the complementary strands (poly(C) and oligo(dC)$_{20}$, respectively, at 0 mg/L (1), 4 mg/L (2), and 8 mg/L (3). The probe concentration in the "accumulation solution" was 1 mg/L, and the hybridization time was 10 seconds. Other conditions duplicated those in FIG. 7.

Figure 9A:
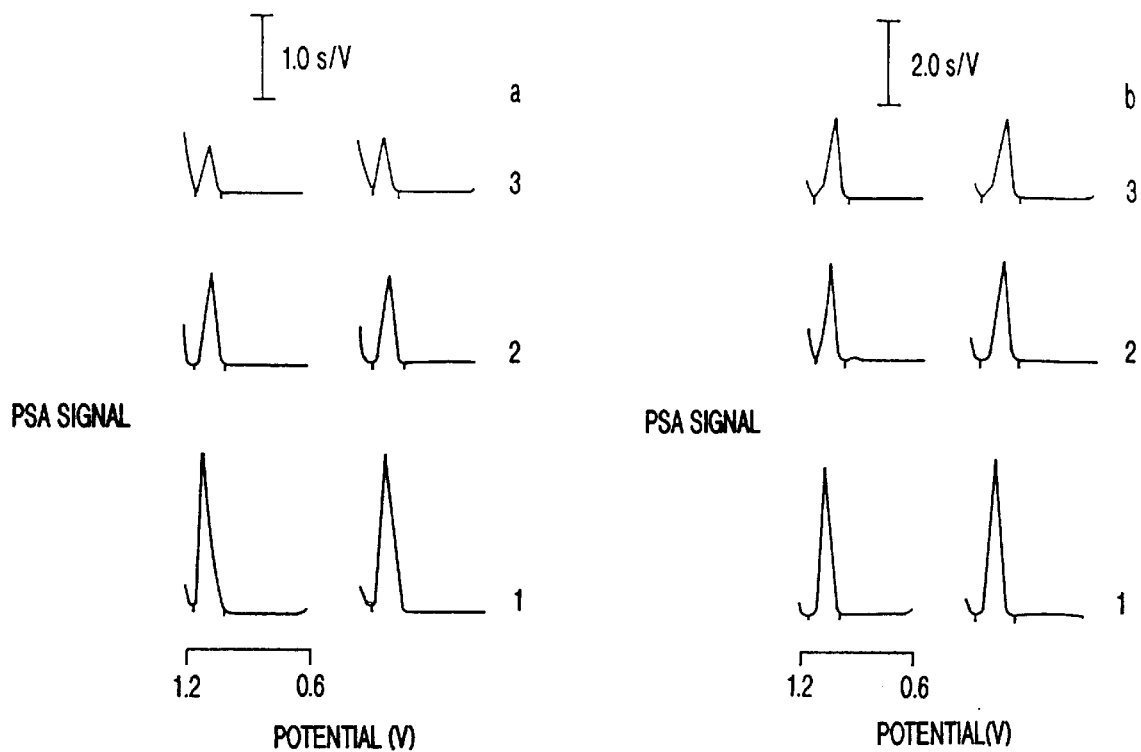
FIG. 9 is a potentiogram obtained at the poly(G)-modified electrode (a) and oligo(dG)$_{20}$-modified electrode (b) in the presence of increasing levels of the complementary strands (poly(C)-modified electrode and oligo(dC)$_{20}$-modified electrode, respectively) at 0 mg/L (1), 4 mg/L (2), and 8 mg/L (3).
Figure 9B:
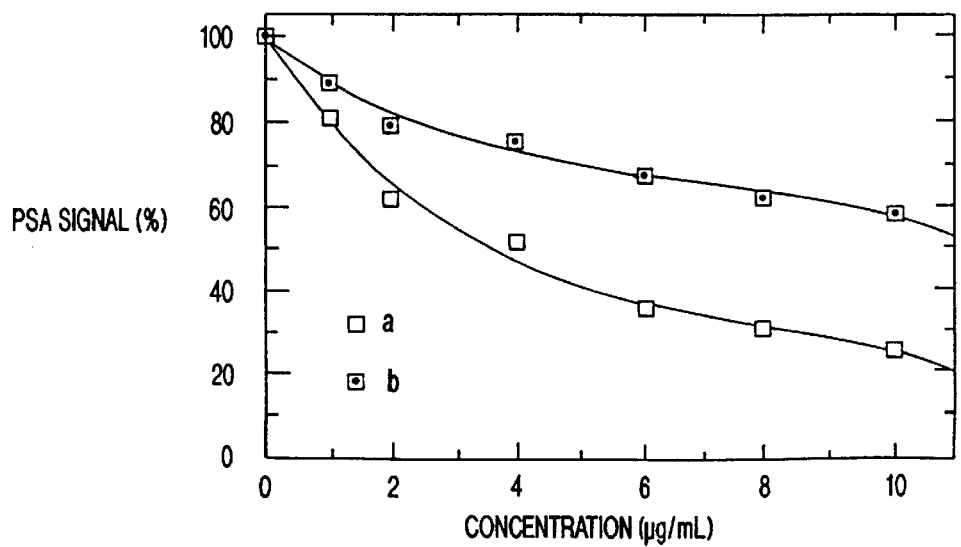

FIG. 9(A) presents the actual response peaks of the potentiograms made during the calibration experiments, and FIG. 9(B) displays the calibration plots obtained at the poly(G)-modified electrode (a) and the oligo(dG)$_{20}$-modified electrode (b) for the target poly(C) and oligo(dC)$_{20}$ strands, respectively. . Both sensors displayed a rapid increase of the probe peak at first (up to 4 mg/L), followed by a slower decline. Yet convenient quantitation of the targets was feasible over the entire 1–10 mg/L range, following extremely short (10 second) hybridization times.

EXAMPLE 9

Figure 10A:
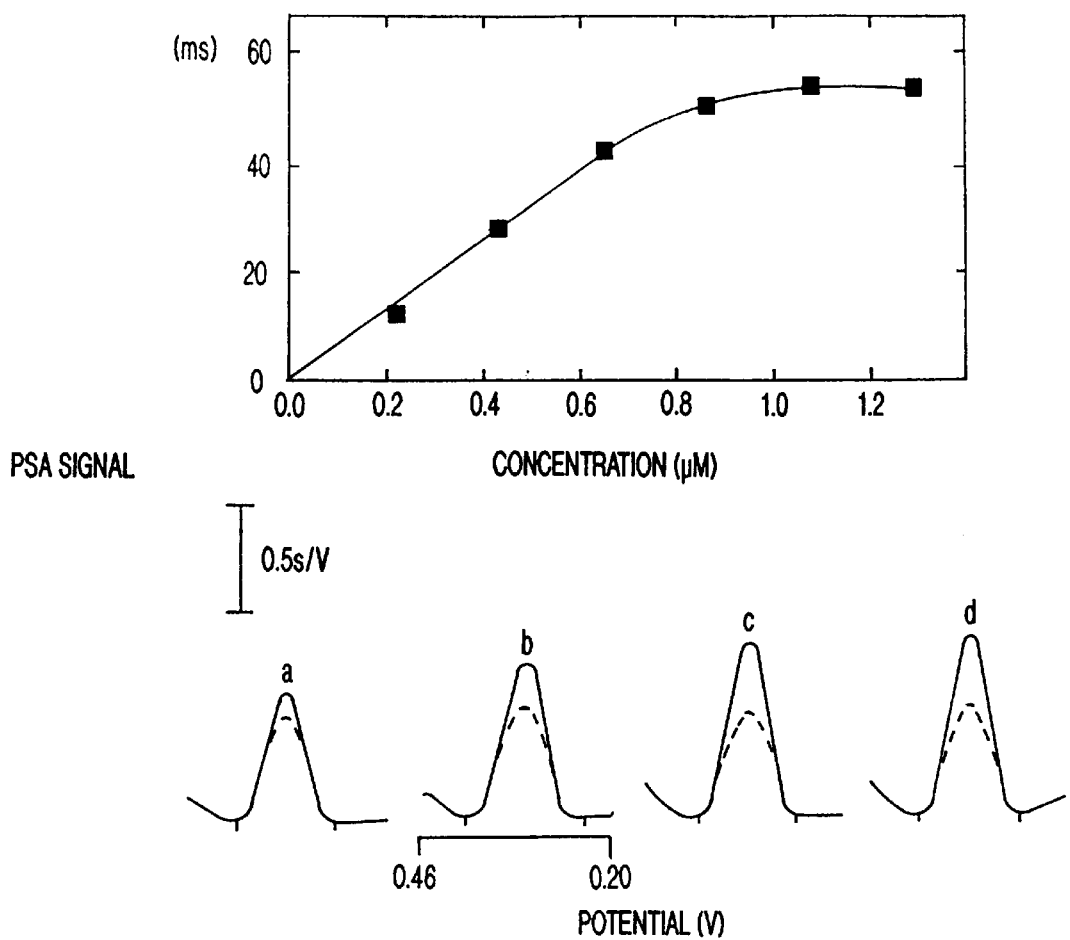
FIG. 10 provides chronopotentiograms of the hybridization response of the thick-film sensor.

FIG. 10 illustrates the response of thick-film sensors. FIG. 10A provides chronopotentigrams (A) for 21-mer HIV DNA (sequence A) with increasing concentrations: 0.2 (a), 0.4 (b), 0.6 (c), and 0.8 (d), using 21-mer HIV DNA (B-sequence) as the probe and Co(phen)$_3^{3+}$ as electroactive indicator, along with a resulting calibration plot from 0 $\mu$M to 1.2 $\mu$M. Dotted lines denote the response of the blank.

Figure 10B:
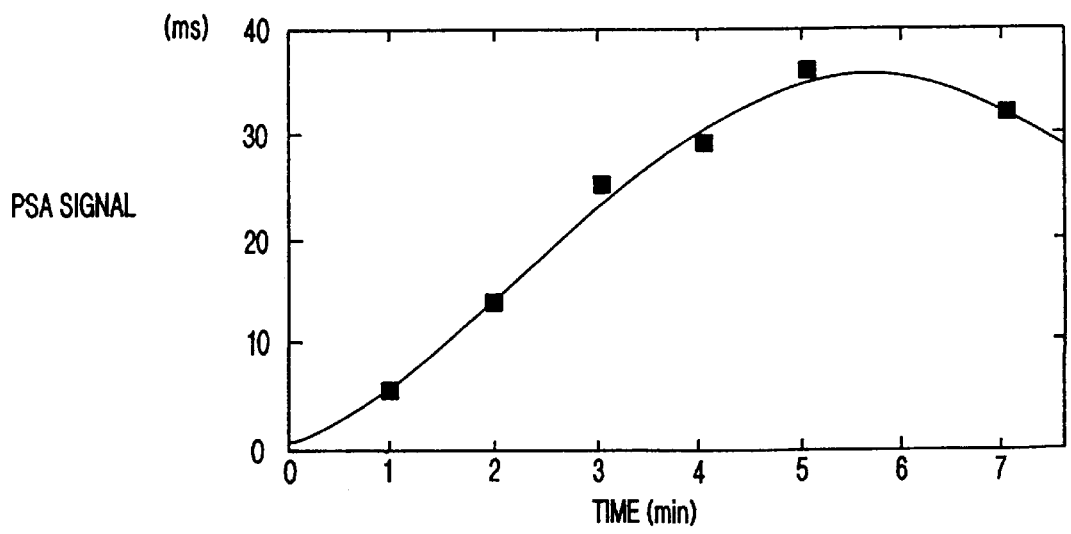

FIG. 10B is a plot showing the effect of hybridization time on the PSA response of 0.5 $\mu$M 21-mer HIV DNA (sequence A). Screen-printed electrode pretreatment and probe accumulation took place under the following conditions: 1 minute at +1.8 V and 2 minutes at +0.5 V in 0.2 M acetate buffer (pH 5.0) containing 0.5 $\mu$M 21-mer HIV DNA (sequence B); hybridization for 5 minutes (A) or for 0 minutes–7 minutes (B) at +0.5 V in 0.02 M phosphate buffer (pH 7.0), 0.75 M NaCl solution containing 0 $\mu$M–1.2 $\mu$M (A) or 0.5 $\mu$M (B) 21-mer HIV DNA (sequence A). Indicator binding was performed for 1 minute at +0.5 V in 0.02 M Tris-HCl and 50 $\mu$M Co(phen)$_3^{3+}$. PSA transduction measurements were in 0.02 M Tris-HCl (pH 7.4) with a current of –8 $\mu$A.

EXAMPLE 10

Figure 11A:
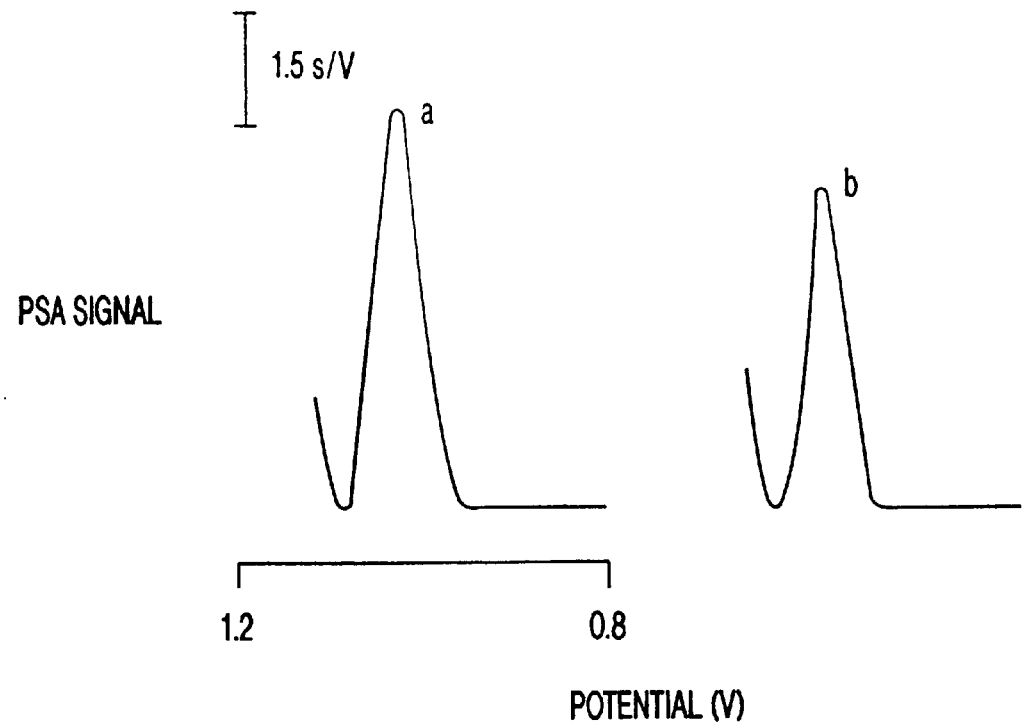
FIG. 11 shows chronopotentiograms for solution-phase (A) and surface-confined (B) calf thymus dsDNA before (a) and after (b) exposure to UV radiation.
Figure 11B:
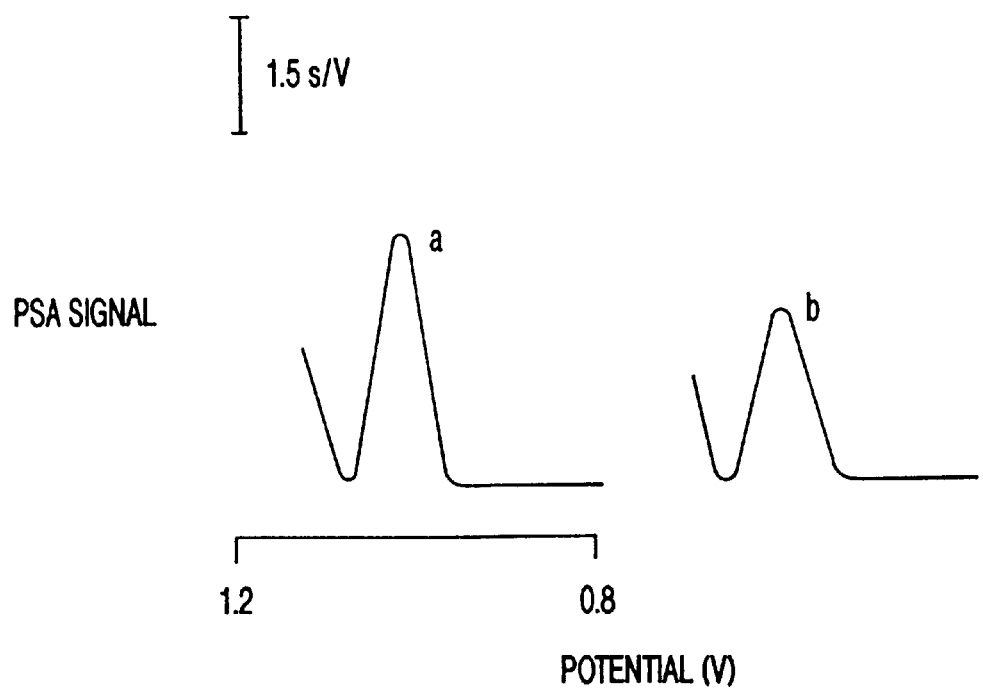

FIG. 11 provides chronopotentiograms for solution-phase (A) and surface-confined (B) calf thymus dsDNA before (a) and after (b) exposure to UV radiation. For obtaining the chronopotentiogram in FIG. 11(A), conditions were the following: sample solution was 5 $\mu$g/mL dsDNA in 0.2 M sodium acetate buffer (pH 5.2); irradiation time was 15 minutes; sample-to-UV lamp distance was 2.5 cm; wavelength was 254 nm; adsorptive stripping potentiometry occurred at the SPEs after 1 minute pretreatment at +1.8 V and 2-minute adsorptive accumulation at +0.2 V; stripping current was +4 $\mu$A. For obtaining the chronopotentiogram in FIG. 11(A), conditions were the following: dsDNA-coated SPEs were covered with a 50 $\mu$L droplet of 0.02 M sodium phosphate buffer (pH 7.0); dsDNA was accumulated from a sodium acetate buffer (0.2M, pH 5.2) containing 5µg/mL ddsDNA by applying +1.8 V for 1 minute, followed by +0.2 V for 2 minutes; irradiation time was 5 minutes; sample-to-UV lamp adistance was 1.0 cm; chronopotentiometric transduction was performed in a blank sodium acetate buffer at a stripping current of +4 µA.

In conclusion, the results of testing demonstrated that screen-printed electrodes are suitable for stripping measurements of nanogram quantities of nucleic acid (e.g., DNA and RNA) sequences, interactions (e.g., with substances such as pollutants or drugs) for analysis of HIV and electro active indicators, and for detection of DNA damage and radioactive indicators. Screen-printed electrodes modified for measuring RNA and DNA have potential application in forensics, clinical diagnostics, industrial testing, agricultural and biomedical research, and biotechnology and molecular biology in general. More particularly, the sequence-selective hybridization chips developed from modification of these thick-film sensors with single-stranded oligonucleotides has further increased the usefulness of the basic thick-film nucleic acid sensor. These DNA-modified strips offer wide range of usefulness in applications involving nucleic-acid interactions with chemical and physical agents (e.g., rapid sensing of DNA damage) or studying other structural transitions (e.g., via enzymatic reactions). In combination with a PSA operation, these chips are also useful for the detection of trace levels of additional types of DNA and RNA. Additionally, using the screen-printing technology, arrays of microband electrodes (coated with different probes) may be fabricated for simultaneous sequence detection of target DNAs. Coupled with the introduction of easy-to-use, miniaturized instruments, such single-use microfabicated electrodes are useful for rapid on-site detection of nucleic acids.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above, and of the corresponding application(s), are hereby incorporated by reference.

What is claimed is:

1. An apparatus for determining nucleic acids comprising:
   a substrate;
   a plurality of screen-printed electrodes on said substrate;
   means for providing electrical contact to at least one of said plurality of screen-printed electrodes;
   means for accumulating a nucleic acid on at least one of said plurality of screen-printed electrodes; and
   means for analyzing a substance by stripping potentiometry at said at least one of said plurality of screen-printed electrodes.

2. The apparatus of claim 1 wherein said plurality of electrodes on said substrate further comprise printing ink on said substrate and said ink is selected from the group consisting of carbon ink and metal ink.

3. The apparatus of claim 2 wherein said metal ink is selected from the group consisting of gold ink and platinum ink.

4. The apparatus of claim 1 wherein at least one of said plurality of electrodes is selected from the group consisting of a reference electrode and an auxiliary electrode.

5. The apparatus of claim 1 wherein at least one of said plurality of electrodes is a working electrode.

6. The apparatus of claim 5 wherein said at least one working electrode is coated with dsDNA and said means for analyzing a substance by stripping potentiometry further comprises means for analyzing interaction reactions of nucleic acid analytes with a target substance.

7. The sensor of claim 6 wherein said target substance is selected from the group of targets consisting of non-microbial pollutants or drugs.

8. The apparatus of claim 5 wherein said at least one working electrode is coated with single-stranded DNA and said means for analyzing a substance by stripping potentiometry further comprises means for analyzing sequence-specific hybridization reactions of nucleic acid analytes.

9. The apparatus of claim 8 wherein said means for analyzing further comprises means for analyzing a substance in the absence of a chemical hybridization indicator.

10. The apparatus of claim 1 wherein said nucleic acid is selected from the group consisting of DNA, scDNA, ssDNA, dsDNA, RNA and tRNA.

11. The apparatus of claim 1 wherein said means for accumulating a nucleic acid comprises a means for adsorbing said nucleic acid onto at least one of said screen-printed electrodes.

12. The apparatus of claim 1 wherein said means for accumulating a nucleic acid on at least one of said plurality of screen-printed electrodes further comprises means for adsorbing a nucleic acid coating on said at least one electrode and means for performing direct potentiometric stripping analysis following oxidation of said adsorbed nucleic acid coating on said at least one electrode.

13. The apparatus of claim 12 wherein said means for performing direct potentiometric stripping analysis further comprises means for performing constant current potentiometric stripping analysis for measuring nucleic acid analytes at said at least one electrode.

14. The apparatus of claim 1 further comprising:
   a hand-held, portable housing means for on-site stripping potentiometry.

15. A method for nucleic acid detection, comprising the steps of:
   accumulating a nucleic acid on at least one of a plurality of screen-printed electrodes on a substrate;
   providing electrical contact to at least one of said plurality of screen-printed electrodes; and
   analyzing a substance by stripping potentiometry at said at least one of said plurality of screen-printed electrodes.

16. The method of claim 15 wherein the substance to be analyzed is a nucleic acid species and further comprising the steps of:
   rinsing said plurality of screen-printed electrodes;
   anodizing said plurality of screen-printed electrodes;
   oxidizing said accumulated nucleic acid by constant current potentiometric stripping analysis; and
   detecting interactions of said adsorbed nucleic acid.

17. The method of claim 15 wherein the step of accumulating comprises accumulating a member selected from the group consisting of ssDNA, dsDNA, scDNA, RNA, and tRNA, and wherein the substance to be analyzed is a nucleic acid species, comprising the further steps of:
   immersing said at least one electrode with said accumulated nucleic acid in a solution containing a target nucleic acid;
   performing a hybridization reaction;

transducing a base-pairing recognition event by potentiometric stripping analysis; and detecting nucleic acid sequences by the selective hybridization reaction.

18. The method of claim 17 performed in the absence of a chemical hybridization indicator.

19. The method of claim 18 wherein the step of detecting comprises detecting HIV-1 DNA in cells.

20. The method of claim 17 wherein the step of detecting comprises detecting DNA damage in cells.

* * * * *